United States Patent [19]

Griffiths

[11] Patent Number: 4,802,243
[45] Date of Patent: Feb. 7, 1989

[54] ACOUSTIC HEADGEAR-SUN VISOR ASSEMBLY

[76] Inventor: John W. Griffiths, 3940 NW. Echo Ct., Portland, Oreg. 97229

[21] Appl. No.: 112,556

[22] Filed: Oct. 26, 1987

[51] Int. Cl.$^4$ ............................................. A42B 1/24
[52] U.S. Cl. ............................................. 2/6; 2/422; 2/423; 2/424; 24/135 N
[58] Field of Search ................. 2/410, 6, 422, 423, 2/425, 15, 10, 12, 13, 209, 417–421, 426, 427, 428, 438, 451–454, 183, 185, 424; 403/344; 24/135 N, 458

[56] References Cited

U.S. PATENT DOCUMENTS

| | | | |
|---|---|---|---|
| 254,473 | 3/1882 | Gates | 24/135 N |
| 1,507,215 | 9/1924 | Spettique | 24/545 |
| 2,428,746 | 10/1947 | Veneklasen | 2/422 |
| 2,568,390 | 9/1951 | Gehrke | 24/458 |
| 2,784,407 | 3/1957 | Ladd | 2/423 |
| 2,875,670 | 3/1959 | Thornton | 2/13 |
| 3,009,158 | 11/1961 | Comeau et al. | 2/14 |
| 3,030,627 | 4/1962 | Rehman et al. | 2/6 |
| 3,108,282 | 10/1963 | Rehman et al. | 2/6 |
| 3,258,534 | 6/1966 | Goldsworthy | 2/422 |
| 3,261,028 | 7/1966 | Coletta | 2/209 |
| 3,268,965 | 8/1966 | Arthur | 24/135 N |
| 3,273,164 | 9/1966 | Thomas | 2/10 |
| 3,284,050 | 11/1966 | De Meyer | 24/135 N |
| 3,430,267 | 3/1969 | Benner | 2/423 |
| 3,661,225 | 5/1972 | Anderson | 2/6 |
| 3,795,014 | 3/1974 | Simpson et al. | 2/209 |
| 3,864,756 | 2/1975 | Desimone | 2/6 |
| 3,943,574 | 3/1976 | Yamaguchi et al. | 2/9 |
| 4,047,249 | 9/1977 | Booth | 2/424 |
| 4,199,823 | 4/1980 | Jenkins et al. | 2/424 |
| 4,479,738 | 10/1984 | Kubnick | 2/10 |
| 4,623,338 | 11/1986 | Larson | 24/135 N |

FOREIGN PATENT DOCUMENTS

| | | | |
|---|---|---|---|
| 640428 | 5/1962 | Canada | 2/424 |
| 483127 | of 1953 | Italy | 2/13 |
| 8200243 | 2/1982 | PCT Int'l Appl. | 2/424 |

Primary Examiner—Harvey C. Hornsby
Assistant Examiner—Joseph S. Machuga
Attorney, Agent, or Firm—Eugene D. Farley

[57] ABSTRACT

An acoustic headgear-sun visor assembly for use by pilots, users of Walkman-type radio and tape deck assemblies, users of noise attenuation devices and the like. The assembly comprises a headpiece including a flat band support member. A split bolt having a bifurcated shank receives the flat band support member. A sun visor is mounted on the split bolt in an angularly adjustable friction fit, enabling shifting it between operative and inoperative positions.

3 Claims, 2 Drawing Sheets

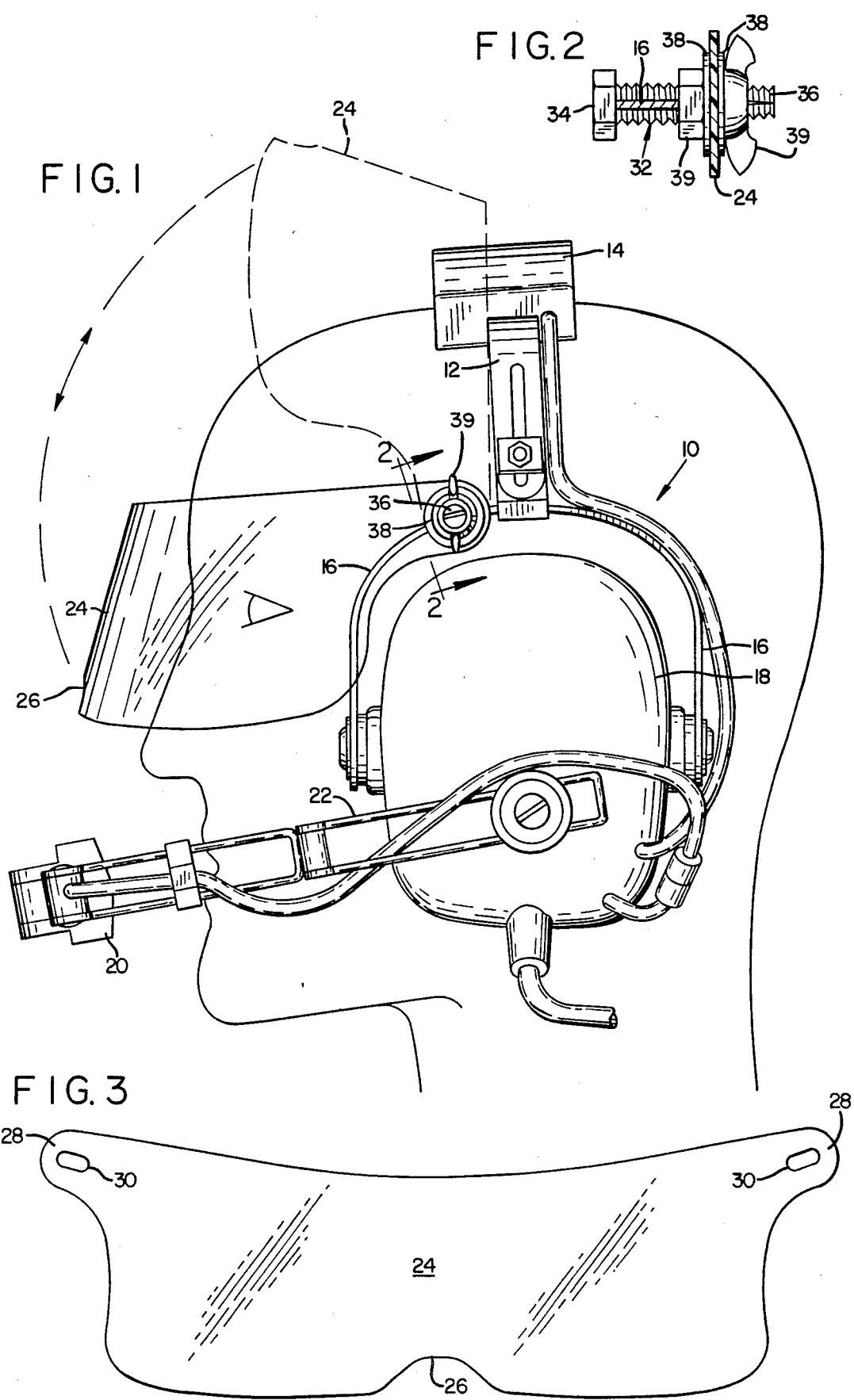

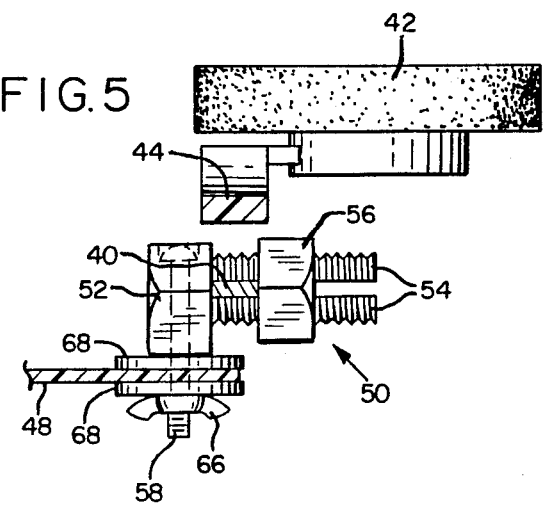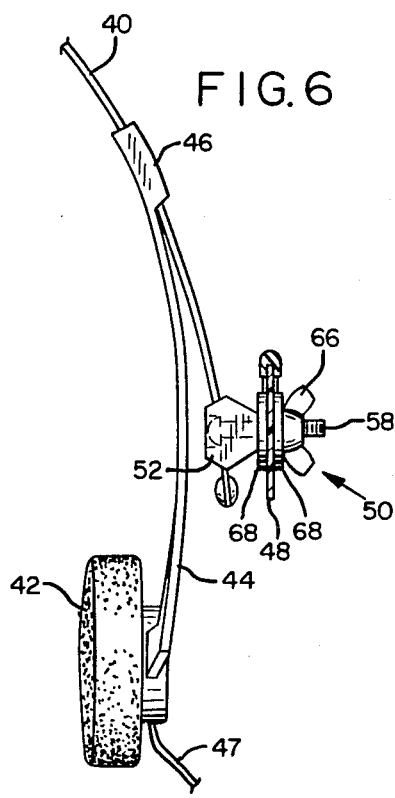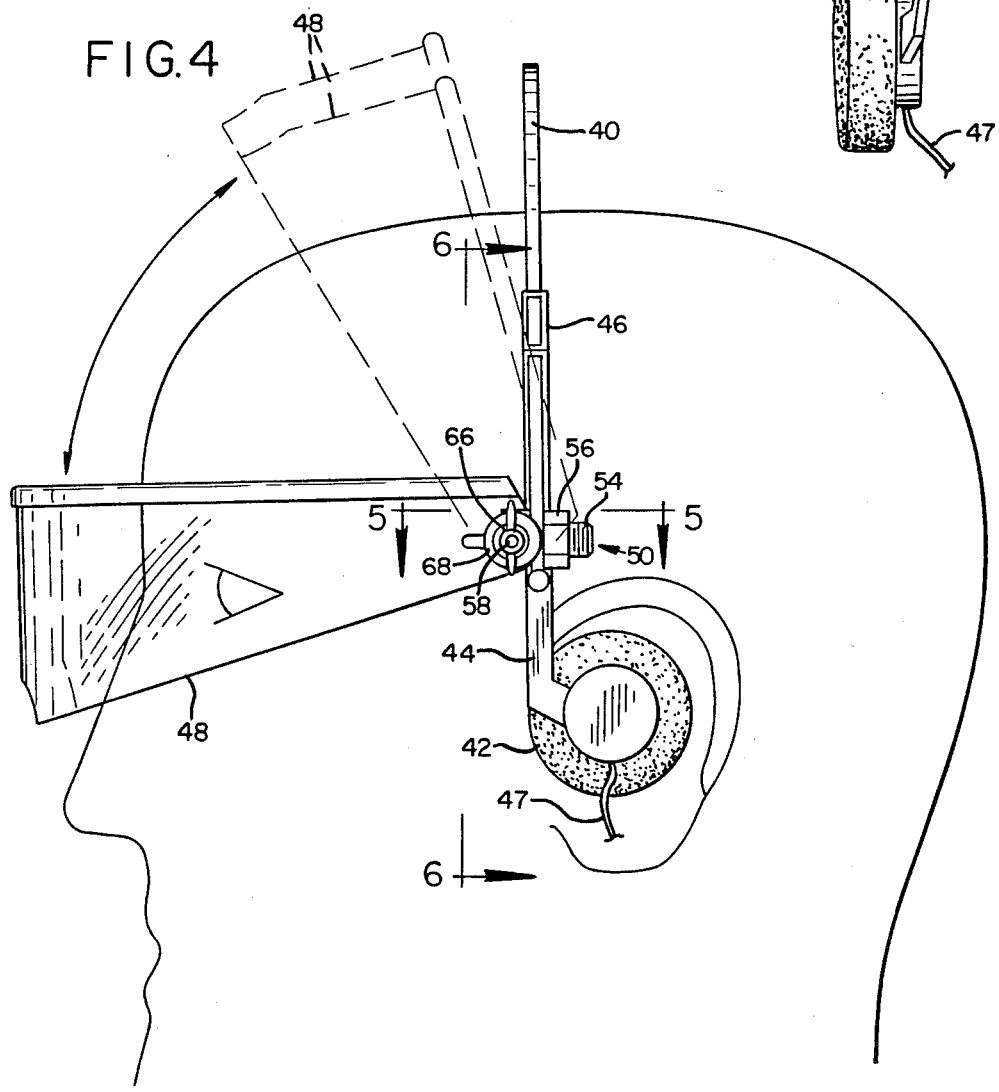

ACOUSTIC HEADGEAR-SUN VISOR ASSEMBLY

BACKGROUND AND GENERAL STATEMENT OF THE INVENTION

This invention relates to acoustic headgear, such as aviators' headphone sets, having a sun visor integrally mounted thereon.

Aviator's headsets consisting of the usual ear phones and microphone supported on a headband do not include in the headset assemblies sunglasses or sun visors functioning to protect the eyes of the aviator from the glare of sunlight, or of artificial illumination. When exposed to glare, the aviator accordingly is under the necessity of removing the headset, putting on a pair of sunglasses or goggles, and then superimposing the headset on the latter. This procedure gives rise to several serious problems.

First, in order to put on his sunglasses, the pilot must remove his headset, put on the sunglasses, and then replace his headset in a position superimposed over the sunglasses. This requires the use of both hands, necessitating removal of the hands from the controls—a dangerous operation, particularly when piloting a helicopter.

With the headset removed, the pilot may miss an important radio call.

Since the headset is superimposed over the sunglasses, the bows of the latter penetrate, and destroy the function of, the earcup seal which is designed to protect the pilot from hearing loss.

Since the headset is superimposed over the sunglasses, the earphones press against the bows of the eyeglasses, causing discomfort and even headache.

Dangerous reflections sometimes develop from light pentrating the sides of the sunglasses and reflecting from the rear surfaces of the lenses.

The bows of the sunglasses present an obstruction which interferes with side vision.

Sunglasses are prone to slide down the nose of the wearer, causing discomfort and requiring the removal of the pilot's hands from the aircraft controls for sunglass adjustment.

The sunglasses being separate from the headset gives rise to the possibility of forgetting the sunglasses on take-off.

It is the general purpose of the present invention to provide a combination acoustic headgear and sun visor assembly for use by pilots and others which assembly is easily and inexpensively fabricated using conventional headgear; which is universally adaptable to various types of acoustic headgear; which affords superior protection to the eyes and ears of the wearer; and which may be provided in various designs, colors and contours to suit the desires and needs of the wearer.

The headgear also is adaptable for use by a wide variety of users, including aviators, helicopter pilots, the users of "Walkman" type radio sets and tape recorders, and industrial workers in noise pollution environments where the use of ear muffs or other noise attenuating devices is required.

Broadly stated, the device of my invention, which achieves the foregoing and other objects, comprises an acoustic headgear-sun visor assembly comprising in combination an acoustic headpiece including a flat headband support member; a split bolt having a bifurcated shank receiving the flat headband support member; a sun visor; and mounting means mounting the sun visor on the split bolt. When thus mounted, the sun visor is always available and has an angularly adjustable friction fit permitting its adjustment between operative and inoperative positions without removal from the headpiece.

THE DRAWINGS

In the drawings:

FIG. 1 is a view in side elevation of the acoustic headgear-sun visor assembly of my invention as applied to aviation-type headgear;

FIG. 2 is a detail view in lonitudinal section taken along line 2—2 of FIG. 1;

FIG. 3 is a plan view of a sun visor which may be a component of the herein described assembly;

FIG. 4 is a view in side elevation, similar to FIG. 1, illustrating the acoustic headgear-sun visor assembly of my invention in a second embodiment, as applied to Walkman type head sets;

FIG. 5 is a fragmentary, detail view, partly in section, taken along line 5—5 of FIG. 4; and FIG. 6 is a fragmentary, detail view, partly in section, taken along line 6—6 of FIG. 4.

DESCRIPTION OF SPECIFIC EMBODIMENTS OF THE INVENTION

FIGS. 1-3 inclusive, illustrate the invention as applied to conventional acoustic aviation headgear.

As shown particularly in FIG. 1, the aviation headgear, indicated generally at 10, comprises an adjustable headband 12 with pad 14.

The lower end of headband 12 is connected to yoke-shaped earphone support members 16. The latter in turn support a pair of conventional earphones, one of which is indicated at 18. A microphone 20 is supported in the usual way on a bracket 22 which, in turn, is mounted adjustably on earphone 18.

The foregoing elements of the assembly are conventional. In accordance with the present invention, advantage is taken of flat band earphone support yoke 16 to support a cooperating sun visor, indicated generally at 24.

The sun visor preferably is fabricated in the desired color and shade from a sheet of clear plastic. It is provided with a nose recess 26 and with a pair of oppositely directed mounting tabs 28, each of which has an elongated perforation 30, FIG. 3.

The sun visor preferably is of the wrap-around variety, which protects the eyes of the wearer from unwanted light reflections and injury from flying particles.

The manner of attachment of the sun visor to flat band yoke support 16 is illustrated in FIG. 2.

A split bolt 32 having a head 34 and a split or bifurcated shank 36 receives an appropriately located segment of yoke 16 between its bifurcations. This mounts the bolt adjustably on the headband in the appropriate location and at the proper elevation.

The bifurcated shank in its entirety is inserted in one of perforations 30 in visor 24. There it is maintained releasably by means of a pair of washers 38 and a pair of lock nuts 39. This mounts the visor on the bolt.

The mounting is such as to render the visor angularly adjustable in a friction fit between the operative, full line position of FIG. 1 and the inoperative, dashed line position of that figure.

The manner in which the headgear-sun visor assembly of the present invention is applied to a Walkman-type radio receiver or tape deck is illustrated in FIGS. 4-6.

As shown in FIG. 4, the conventional Walkman set comprises a flat, elastic headband 40, and a pair of earphones, one of which is indicated at 42. Each earphone is mounted on an earphone bracket 44 which in turn is mounted slidably and frictionally on headband 40 by means of a frictional slide connector 46.

An electrical lead 47 connects the earphone to the radio or tape recorder.

In this assembly, advantage is taken of flat headband 40 to mount a wrap-around sun visor 48 on the headgear in the proper position relative to the eye of the user. The means by which this is accomplished is illustrated particularly in FIGS. 5 and 6.

A split bolt 50 having a head 52 and a split or bifurcated shank 54 receives headband 40 between the bifurcations of split shank 54. There is clamped releasably in place by means of a lock nut 56. This mounts the split bolt on the headband.

Head 52 of the split bolt is provided with a transverse perforation completely through the head. This is dimensioned to receive a bolt 58 with associated nut 66. The bolt mounts an end of visor 48, clamped releasably in place by means of nut 66 and a pair of lock washers 68.

The visor thus is mounted on the bolt in an angularly adjustable friction fit enabling shifting it between the solid line, use position of FIG. 4 and the dashed line, inoperative position of that figure.

The assembly is further adapted for use in conjunction with ear muffs or other noise attenuators, which would replace earphones 18 of the embodiment of FIG. 1, or the earphones 42 of the embodiment of FIG. 4 in a self-evident manner.

Having thus described in detail a preferred embodiment of the present invention, it will be apparent to those skilled in the art that various physical changes may be made in the device described herein without altering the inventive concepts and principles embodied. The present embodiment is therefore to be considered in all respects as illustrative and not restrictive, the scope of the invention being indicated by the appended claims.

I claim:

1. The acoustic headgear-sun visor assembly comprising in combination:
    (a) an acoustic headpiece configured to extend laterally over a head and including a flat band support member at each side of the headpiece,
    (b) a pair of split bolts each having a bifurcated, externally threaded shank receiving the flat band support member in the slot between the bifurcations,
    (c) a nut threaded on said bifurcated shank releasably securing said flat band support member between said nut and the base of said slot,
    (d) sun visor means, and
    (e) mounting means mounting the sun visor means on the split bolt.

2. The acoustic headgear-sun visor assembly of claim 1 wherein each flat band support member is a yoke-shaped flat band support member supporting an earphone, the sun visor means comprises an arcuately bent length of clear plastic having a perforation adjacent each end, each perforation receiving the threaded shank of one of the pair of split bolts, and the sun visor mounting means comprises lock nut means on the threaded shank of each split bolt securing the sun visor means thereto in an angularly adjustable friction fit.

3. The acoustic headgear-sun visor assembly of claim 1 wherein each split bolt has a transversely perforated head, the sun visor means comprises an arcuately bent length of clear plastic having a perforation adjacent each end, and the sun visor mounting means comprises nut and bolt means penetrating both the perforation in the split bolt head and the associated perforation in the sun visor means, thereby locking the sun visor means to the split bolt head in an angularly adjustable friction fit.

* * * * *